United States Patent [19]

Giampapa

[11] Patent Number: 5,246,463
[45] Date of Patent: Sep. 21, 1993

[54] SENSATE AND SPACIALLY RESPONSIVE PROSTHESIS

[76] Inventor: Vincent C. Giampapa, 89 Valley Rd., Montclair, N.J. 07042

[21] Appl. No.: 840,915

[22] Filed: Feb. 21, 1992

[51] Int. Cl.⁵ .............................................. A61F 2/70
[52] U.S. Cl. .................................... 623/24; 623/57
[58] Field of Search .................. 623/24, 25, 57, 64, 623/60, 62; 600/28

[56] References Cited

U.S. PATENT DOCUMENTS

| | | | |
|---|---|---|---|
| 2,656,545 | 10/1953 | Conzelman et al. | 623/57 |
| 3,751,733 | 8/1973 | Fletcher et al. | 623/24 |
| 3,820,168 | 6/1974 | Horvath | 623/24 |
| 4,112,596 | 9/1978 | Fletcher et al. | 623/24 X |
| 4,770,662 | 9/1988 | Giampapa | 623/24 |
| 5,037,376 | 8/1991 | Richmond et al. | 623/24 X |

FOREIGN PATENT DOCUMENTS 2376657 9/1978 France ................ 623/24

Primary Examiner—Randall L. Green
Assistant Examiner—D. Willse
Attorney, Agent, or Firm—M. K. Silverman

[57] ABSTRACT

A sensory input discrimination system for use with a prosthetic limb such as the prosthetic lower arm includes touch pressure transducers such that information regarding pressure upon portions of the prosthesis, temperature therein, and changes in position of joints thereof will result in a sonic frequencies of characteristic pattern. Such characteristic sonic frequency patterns are communicated to the sonic proximity vibratory receptors existent upon a bone stump of an amputation site correspondent to the connection of the prosthetic limb. Such receptors will resulting generate neural impulses having a signal pattern correlating to the sonic output patterns of a system power unit that will travel from the stump to the posterior columns of the spinal cord and, therefrom, to the brain. Discrimination of such impulses will be accomplished to enable recognition of pressure, upon the prosthesis. Information relative to temperature and spatial orientation of joints of the prosthesis is, via audio chip technology, provided to the ear. One musical octave will correspond to the extent of flexure of one joint while another octave will correspond to extent of flexure, or up/down position, of another joint.

12 Claims, 8 Drawing Sheets

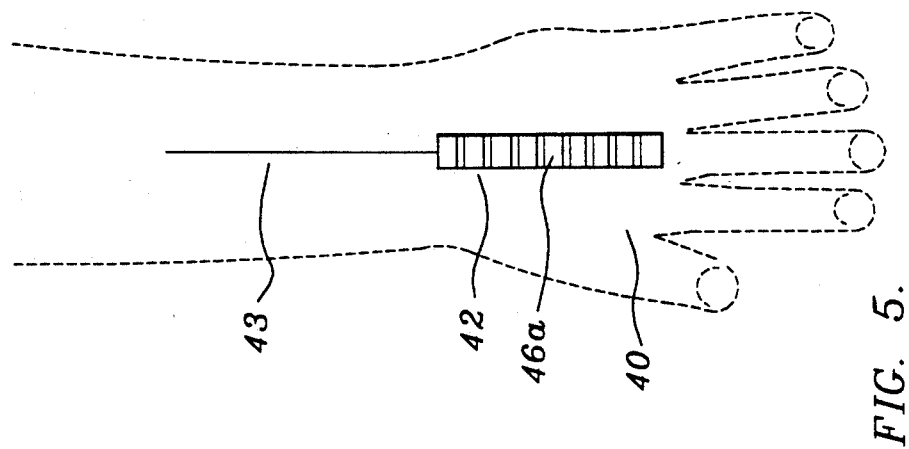
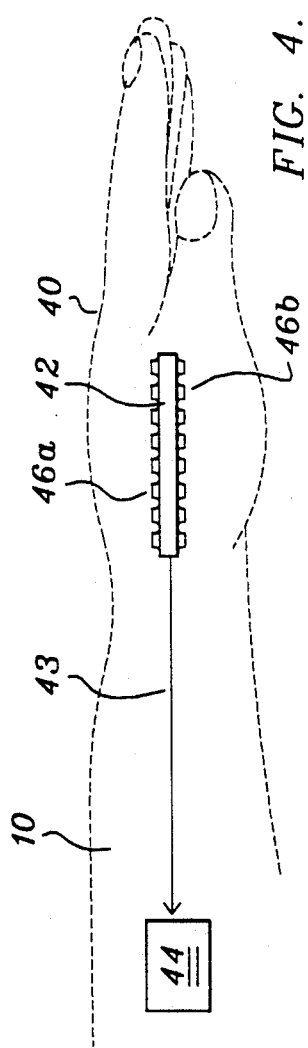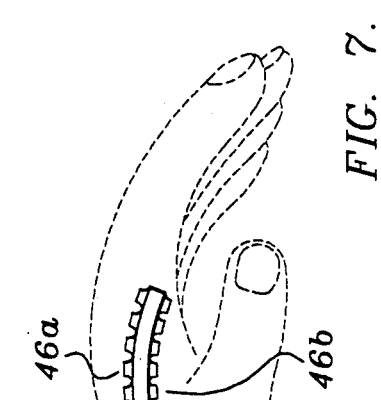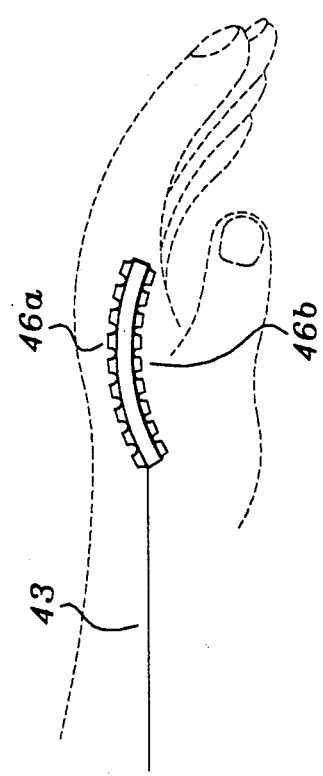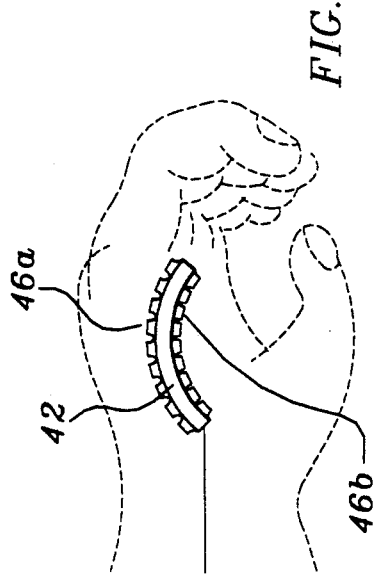

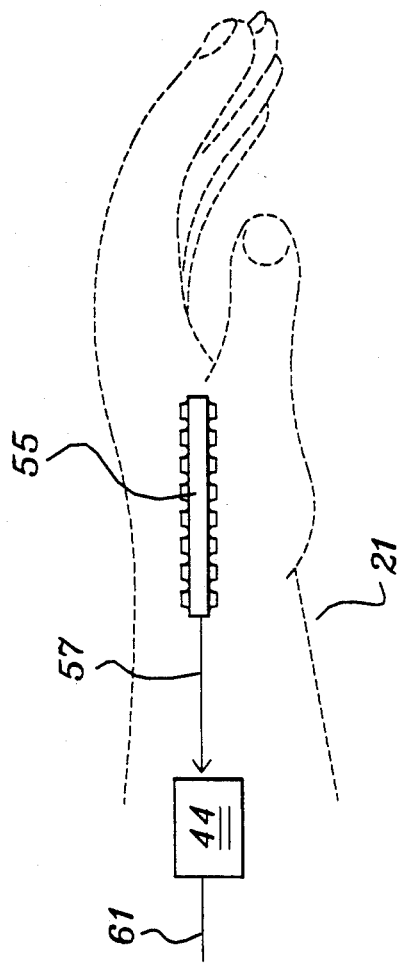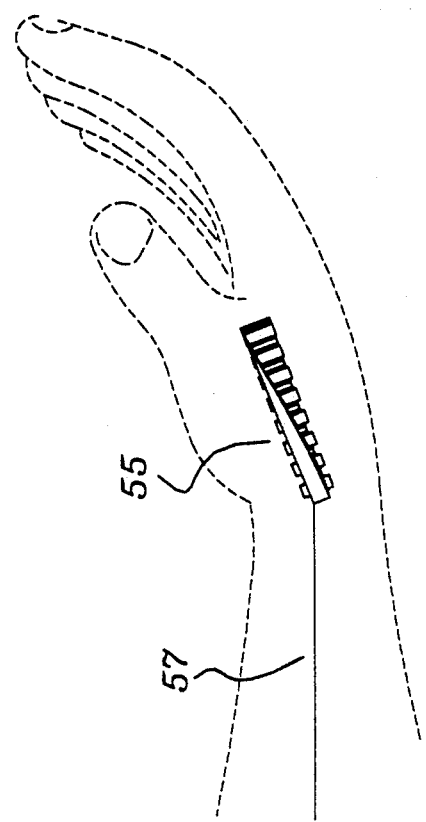

SENSATE AND SPACIALLY RESPONSIVE PROSTHESIS

BACKGROUND OF THE INVENTION

This invention is an improvement of my earlier invention as set forth in U.S. Pat. No. 4,770,662 (1988), entitled Sensate Vibratory Prosthesis. That invention was concerned with the provision to the so called posterior columns of the spinal cord and, therefrom, to the brain, information respecting the digit (finger) location of pressure-related stimuli. In other words, the object of said invention was to provide information to the user of a limb prosthesis regarding the existence of touch pressure in excess of a predetermined level, upon respective digits of the hand and, more particularly, to advise the user as to which particular digit was subject to such excessive pressure or is touched or another digit.

The present invention expands upon said invention in a number of material ways. Firstly, the communication of pressure and touch related information, while still providing indications corresponding to particular digits of a prosthetic hand or limb, includes an analog characteristic such that the level of the pressure, in addition to the mere location thereof, may be sensed.

Further, the instant invention can provide to the user analog information regarding temperature, above a predetermined level, upon various parts of the prosthesis.

Further, and of primary importance to the instant invention, information, preferably in the form of musical notes or ranges thereof, representing combinations of signals, is provided. Audio chips within a hearing-aid like unit would such thereof, to the ear relative to the spatial or orthotic orientation of the hand, wrist, elbow, or combination thereof.

A long standing problem in the prior art of limb prosthesis has been that, other than by visual observation by the user, there exists no sense of feeling or other means by which a prosthesis user can determine the degree of openness or closure (generally termed flexure) of a prosthetic hand, wrist or elbow. Such information is useful and is particularly helpful in situations where one is not able to constantly observe the position of the hand or elbow as, for example, where the prosthesis user is holding an object, such as a bag of groceries or when it is dark. In such situations, it is important for the user to have a means, other than through direct visual observation of the joint or surface, of determining the extent of openness or flexure of the joint or surface.

SUMMARY OF THE INVENTION

The instant invention constitutes a sensory input location discrimination system for use with a prosthetic limb. The categories of sensory input for which information is provided include (a) pressure in excess of a predetermined level upon respective parts, such as the fingers, of a prosthetic limb, (b) temperature in excess of a predetermined level and (c) spatial orientation of joints, such as joints of the hand, wrist and elbow in the prosthesis. Sonic frequency generators having characteristic frequencies, amplitudes, and pulse widths are provided to communicate information respecting pressure, extent of joint flexure, and temperature with respect to different areas of the prosthesis. Electrical communication between each frequency generator and its pressure and/or temperature sensor are open in the absence of sufficient contact pressure or temperature and are closed in the presence of actuating pressure or temperature. Such electrical communication will generate a discrete sonic frequency output, over an analog range from that area of the prosthesis to which contact pressure has been applied.

A surgical connection is made of the amplified sonic signals into the proximity of vibratory receptors of a bone stump at an amputation site corresponding in location to the connection of the prosthetic limb. Said receptors will generate a neural impulse, having a signal pattern of frequency and amplitude corresponding to the output signals of said power unit, which neural impulses travel from the bone stump to the posterior columns of the spinal cord and, therefrom, to the brain where discrimination of such neural impulses can be readily accomplished to thereby recognize the location of activating pressure and the level of pressure.

Information relative to temperature and spatial orientation of joints of the prosthesis is, via audio chip technology, provided to the ear. One musical octave will correspond to the extent of flexure of one joint while another octave will correspond to extent of flexure, or up/down position, of another joint.

It is accordingly an object of the instant invention to provide a prosthetic device having improved sensing and control capabilities.

It is another object to provide a prosthetic device having a capability of determining which area thereof is subject to pressure or temperature and at what level.

It is a further object of the present invention to provide a prosthetic device having means for advising the user, on a real time basis, regarding the extent of flexure of joints of the prosthesis, without requirement for visual observation of such joints to obtain such information.

It is a yet further object to provide a sensing and control means for a prosthesis which will render more meaningful and useful existing developments in parameter sensing and servo-control.

The above and yet other objects and advantages of the invention become apparent from in the hereinafter set forth Detailed Description of the Invention, the Drawings, and Claims appended herewith.

BRIEF DESCRIPTION OF THE DRAWINGS

FIG. 4 is a schematic view of a prosthetic hand, in open position, equipped with a geometry-dependent sensing element.

FIG. 5 is a top view of FIG. 4.

FIG. 6 is a view, similar to FIG. 4, however, showing the prosthetic hand in a rest position.

FIG. 7 is a view, similar to the view of FIG. 6, however, showing the hand in a gripping or flexure position.

FIGS. 8 and 9 are views of the wrist of the prosthesis in down and up positions respectively.

DETAILED DESCRIPTION OF THE INVENTION

All prior art known to the inventor, other than his own above referenced U.S. Pat. No. 4,770,662, pertains to the transmission of signals to the skin covering whatever tissue (typically skin) that may exist at the amputation site. In distinction, the instant invention makes use of a vibrational signal, transmitted to the bone stump nearest to the amputation site. A sonic contact, i.e., a metal screw, is placed within the amputation site. Such a sonic contact, in combination with vibratory receptors that have been found to be a part of the anatomy of the bone stump of an amputation site, act to convert vibrational or sonic signals into neural pulses which are transmitted to the posterior columns of the spinal cord and, therefrom, to the brain. This represents a different neurologic circuit than is employed in the prior art.

Figure 1:
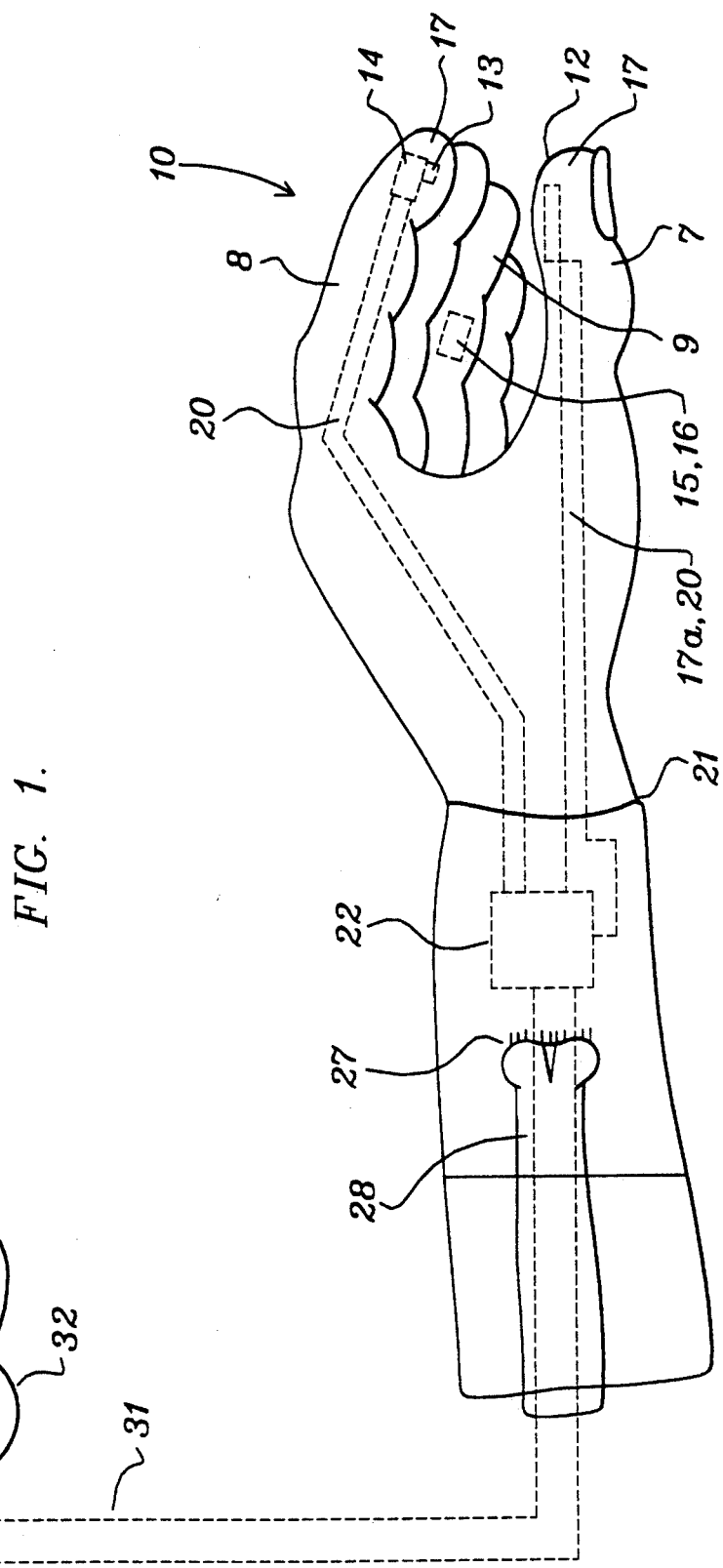
FIG. 1 is a conceptual view of the prosthetic device including therein sonic frequency generators for localizing the site of tactile stimuli, the view including a cross-section of neural pathing to the posterior columns of the spinal cord.

With reference now to the Drawings in which like references characters designate like or corresponding parts, there is illustrated in FIG. 1 an electromechanical prosthesis 10 of any suitable design since prosthetic devices, such as a lower arm including an elbow and hand, are well known and form no significant part of the instant invention. A detailed description of prosthesis 10 including the internal servomechanisms which make possible movement of the fingers, hand and elbow, is omitted in the interest of brevity. Rather, it is sufficient to understand that prosthesis 10 includes suitable mechanical drive units (not shown) including servomotors, servomechanisms and the like for enabling reciprocating operation of the hand and elbow and rotational movement of the wrist, as is taught in the prior art. Further, it is to be understood that the instant prosthesis 10 may, if desired, assume the configuration of a foot, as well as other parts of the anatomy, to which the principles of the invention may be equally applied.

The digits of prosthesis 10 are designated as thumb 7, index finger 8 and end digits 9. Within the distal ends thereof there is, in addition to whatever sensing means may be indicated or suggested in the prior art, provided the instant pressure sensing means of the invention, each of which comprises a two part structure. More particularly, thumb 7 is provided with a pressure transducer 11 and a sonic frequency generator 12. Similarly, index finger 8 is provided with a pressure transducer 13 and a sonic frequency generator 14. Similarly, end digits 9 are provided with pressure transducers 15 and sonic frequency generators 16.

Figure 2B:
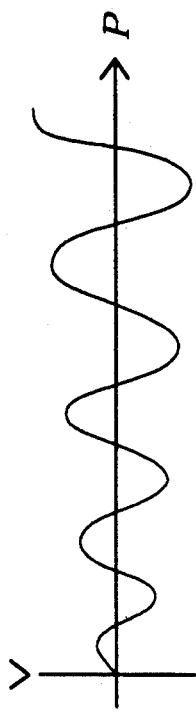
FIGS. 2A to 2E are a series of the signal patterns relating to pressure
Figure 2A:
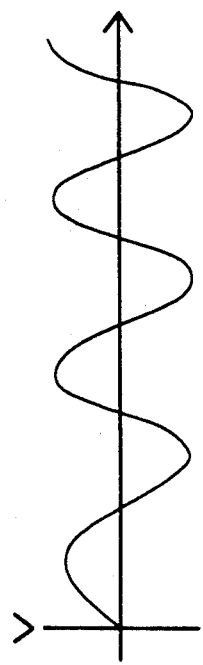

The said sonic frequency generators 12, 14, and 16 refer to sonic vibrating elements, the circuit of which (see FIG. 3) is closed upon the application of presure to a particular digit. Pressure upon a digit is hereby sensed by the transducers which then actuate the sonic frequency generators. In other words, the pressure transducers operate to initiate the vibrating of a sonic frequency discreet to the particular digit to which the pressure has been applied. The basic sonic frequency for the pressure of ordinary touching is shown in FIG. 2A.

In an improvement over my said U.S. Pat. No. 4,770,662, the amplitude (Voltage V) of the sonic frequency will increase on an analog basis, after said circuit has been closed, such that the user of the prosthesis will be advised not only that a digit has made contact with a surface but, as well, the extent to which pressure applied to said digit exceeds the pressure of ordinary teaching. This analog change is shown in the signal illustrated in FIG. 2B.

In the study of neurological factors, it has been determined that three represents the optimum number of stimuli which the brain can employ for purposes of differentiation before becoming confused with sensory overload. Bearing this in mind and, as well, to insure reliability in the sensing process, it has been determined that the selected three sonic frequencies should be separated logarithmically, which is to say that each frequency should be substantially double the preceding frequency.

Employing such criteria, it has been found that frequency generator 12 of thumb 7 should employ a frequency of approximately 100 cycles per second (cps), that frequency generator 14 of index finger 8 should employ a frequency of 300 cps and that frequency generator 16 in end digits 9 should employ a frequency of 700 cps.

With the above frequency increments of each between the three pressure sensing elements, it has been found that the brain can readily differentiate such respective sonic frequencies without sensory overload. Given such discrimination the use of the system can determine not only the digit upon which pressure is impacting but, as well, the relative amount of pressure by virtue of the amplitude of the resultant sonic frequency. It is noted that an analog pressure transducer, such as a piezo-crystal, may be used in lieu of a digital transducer.

Figure 2D:
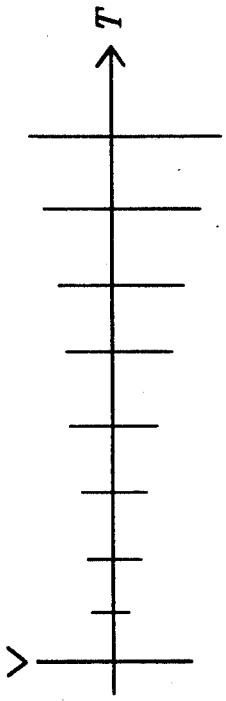
Figure 2C:
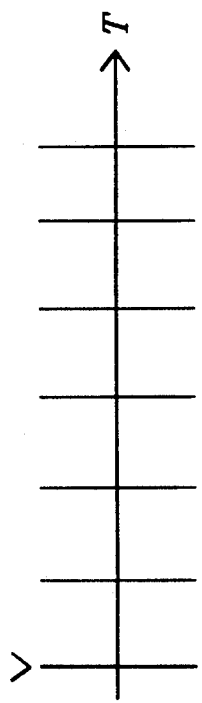
Figure 2E:
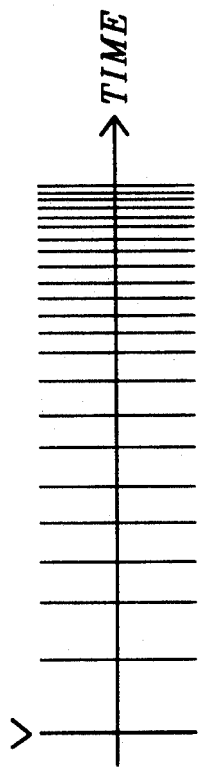

Any of the above referenced pressure transducers may be provided with thermal sensors 17 (see FIG. 1), which will generate, in said sonic frequency generators, signals having a different pattern. For example, the outputs of the pressure transducers would produce an essentially sinusoidal waveform (see FIGS. 2A and 2B), while the output 17A of thermal sensors 17 would produce a series of narrow pulses in which an increase in amplitude or frequency of the pulses would be a function of the temperature (See FIGS. 2C to 2E). The outputs of said thermal sensor are provided to the below described audio chip subsystem and in turn, to the ear of the user.

Figure 3:
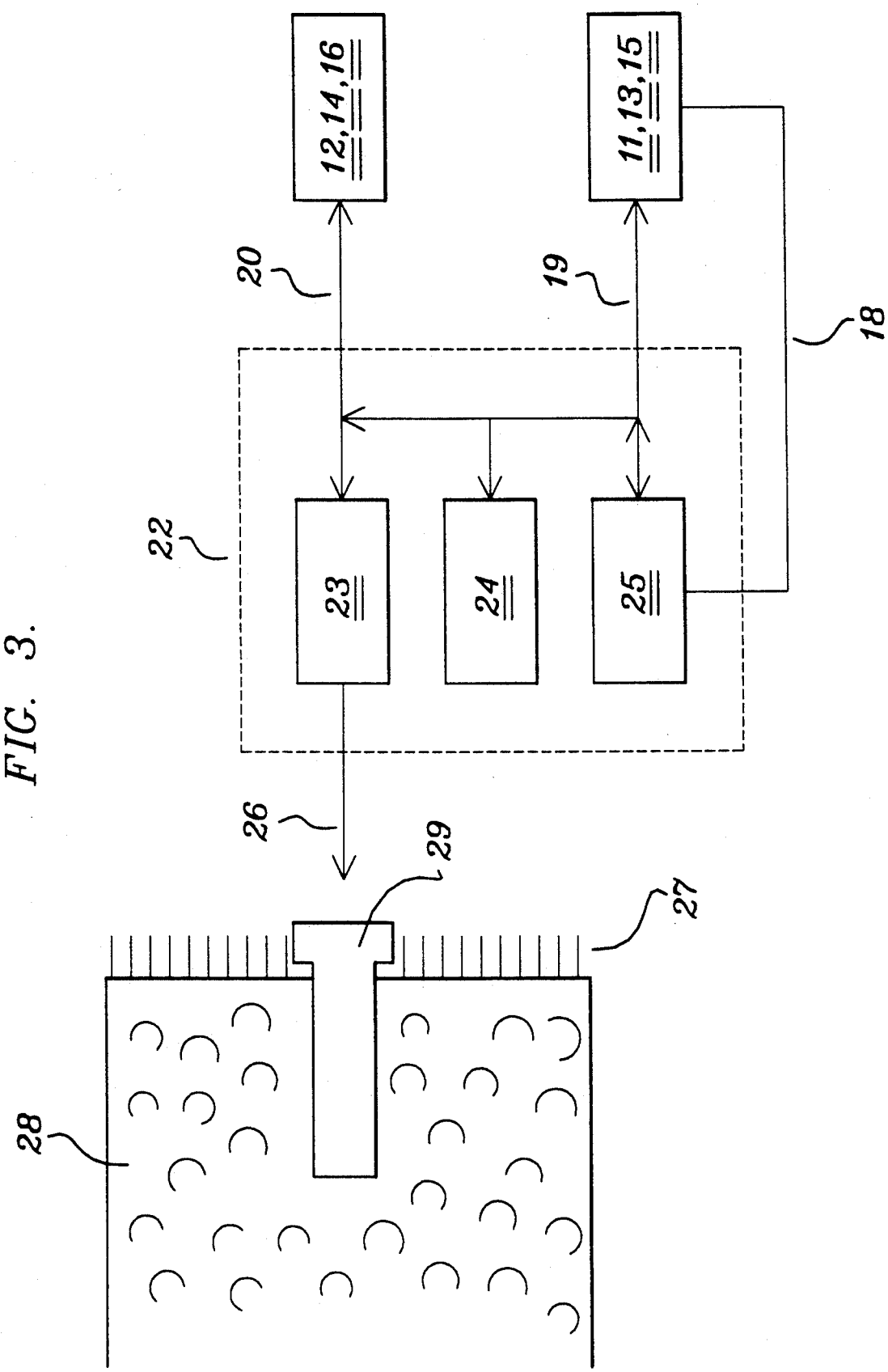
FIG. 3 is a schematic block diagramatic view of the circuitry employed in the portions of the vibratory prosthesis relative to the sensing of pressure and temperature.

With further reference to FIGS. 1 and 3, it is seen that the output of said frequency generators, and pressure transducers, are fed to pathways 18 thru 20 from the prosthesis to a power system 22. In power system 22 (see FIG. 3) there is provided a frequency amplifier 23 by which the outputs of said frequency generators and pressure transducers are amplified. Also, included in power system 22 is a power source (such as a battery) 24 and a voltage amplifier 25. The sonic wave form output of the frequency amplifier 23 is transmitted, through an output 26, to the sonic proximity of a sonic contact 29, i.e., a metallic screw, and to vibrating receptors 27 of bone stump 28 both of which are, as above noted, a part of the anatomy of an amputation site.

It is to be understood that, through research, it has been determined that when said vibrating receptors 27, as opposed to the skin of the tissue surrounding the amputation site, are sonically stimulated, neural pulses will travel from said bone stump 28, through nerves 31 (see FIG. 1) to the posterior columns 34 of the spinal thalamic tract 33 and, therefrom, to the brain.

The stimulation of the posterior columns of the spinal tract differs from prior art efforts in which stimulation from sensors within the prosthesis is communicated only to the skin. In such stimulation of the skin or adjoining tissue, other than the bone stump, neural impulses are able only to reach anterior area 32 (see FIG. 1) of the spinal tract 33. Through experimentation it has been determined that the usage of the posterior columns 34 comprises a far superior avenue in terms of capacity to use and process information from sensors within a prosthesis. Accordingly, the methodology of communicating the output 26 of power system 22 to said vibratory receptors 27 of bone stump 28 represents a superior means of communication of sensory information from a prosthesis to the brain of a user of the prosthetic device.

Already documented clinical studies have shown that a user is able to, as above noted, discriminate not only between frequencies individually but, as well, between combinations thereof. Further, it has been determined that the learning curve in the use thereof is minimal such that the instant prosthetic sensing system will not only render it possible for the user to discriminate between digits receiving pressure but will permit a more rapid learning process by the prosthetic user in regard to how the prosthesis in general should be used in that the sensory end of organs in the cutaneous region of the stump have been found to be a more satisfactory transmitter of neural pulses (neurons) than is the skin. As such, through the use of a completely different anatomical circuit, primary sensory discrimination, not only in respect to individual digits, but of various other forms of specific information, generated by and within the digits and other parts of the prosthesis, may be improved.

A further variation by which my instant invention represents an improvement over my said U.S. Pat. No. 4,770,662, resides in the ability of my system to sense spatial orientation of parts of a prosthetic device and, more particularly, to sense the degree of twisting (pronation and supination) or flexure, or lack thereof, of the hand and/or wrist and/or elbow portions of the prosthesis.

With reference to FIGS. 4 through 7, it is noted that a prosthetic hand 40 of said prosthesis 10 is provided with a solid state electronic element 42 in which the electrical output characteristics thereof will vary as a function of geometric change in the surface thereof and thereby of hand 40.

There exist many suitable solid state components having such properties. For example, one may employ components having electrical properties, such as resistance, capacitance, or inductance that will vary as a function of changes in geometry. However, with respect to one embodiment of this invention, there is contemplated, per the views of FIGS. 4 through 7, the use of a so-called piezopolymeric element, this being a piezoelectric component in which the electrical output thereof varies as a function of pressure upon various surfaces thereof. Such elements are taught and described by Granicher, pp. 265 to 271, *Solid State Source Book*, McGraw-Hill, 1990, and in numerous other texts and papers on piezoelectricity.

As may be noted in the progression views of FIGS. 4, 6, and 7, the lower surface 46b of the element 42 is subjected to increasing pressure, i.e., increased compression, as a function of the degree of flexure of the prosthetic hand 40, such that the greatest electrical output will occur in the flexure condition of FIG. 7 while the least degree of electrical output upon surface 46b will occur in the open condition shown in FIG. 4. An intermediate degree of output will occur in the rest position shown in FIG. 6.

It is also noted that a top surface 46a of piezoelement 42 is stretched as a function of the degree of closure of prosthetic hand 40. Accordingly, the electrical output thereof will decrease as a function of degree of flexure. Accordingly, the difference in electrical outputs between the output of the respective upper and lower surfaces, that is, between the compression mode of surface 46b and the stress mode of surface 46a, is a significant electrical output. A piezoelectric element is particularly suitable in that even the smallest change in geometry of a piezoelectric structure will result in a change in the internal ionic structure of its molecules with a resultant measurable change in the electrical output characteristic thereof.

There are known today in the art so called piezoelectric ceramics (typically formed of barium titanate), piezoelectric resonators making use of crystalline structures, and piezoelectric vibrators in which changes in the reference vibration of the element will provide a characteristic electrical output.

Electrical output 43 from element 42 is provided to an audio chip assembly 44 described below.

In FIGS. 8 and 9 are shown a piezo-element 55 implanted in the wrist 21 of the prosthesis. Therein torsional force existing on element 55 in the supination (down) position will produce a measurable differential versus the up or propenation position.

Figure 12:
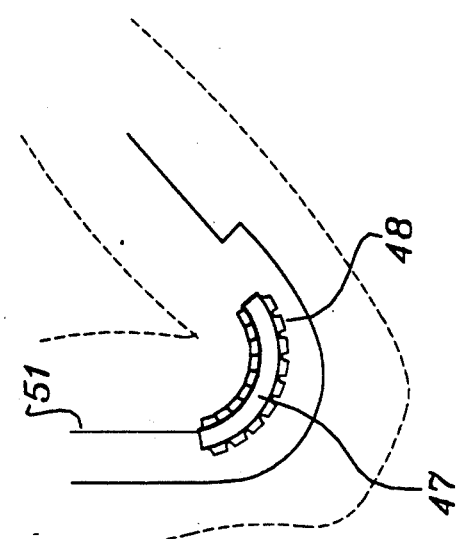
FIG. 12 is a view, similar to the view of FIG. 11, however, showing the elbow of the prosthetic limb in flexure.
Figure 11:
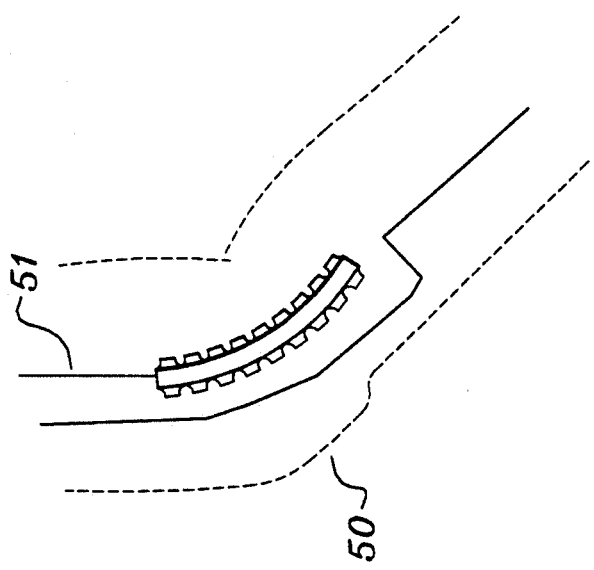
FIG. 11 is a view, similar to the view of FIG. 10, however, showing the prosthetic elbow at rest.
Figure 10:
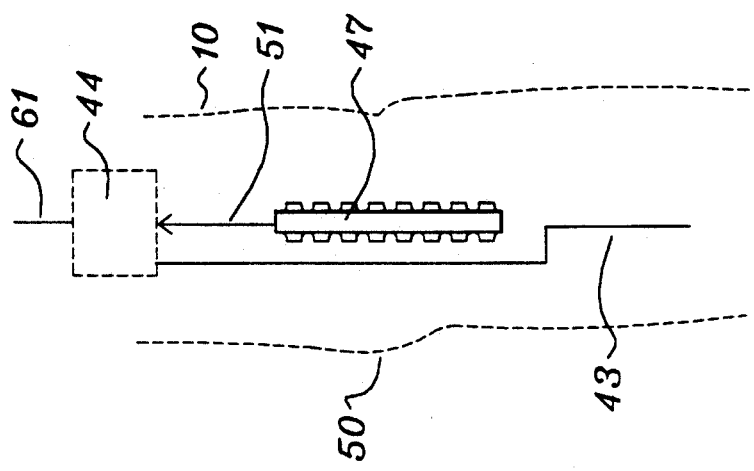
FIG. 10 is a schematic view showing a prosthetic elbow, in open position, equipped with a geometry-dependent sensing element.

With reference to FIGS. 10 through 12, there is shown the use of a piezo-element 47 within an elbow 50 of the prosthetic device 10. In said figures, as in the case of said FIGS. 4 through 9, the piezo-element will provide a characteristic electrical output as a function of the degree of change in geometry thereof, such change in geometry corresponding to the extent of flexure of the joint of the prosthesis which is of interest. Electrical output 51 is provided to power system 44, per the discussion of FIGS. 13 and 14 below.

It is to be appreciated that, as an alternative to the use of piezo-electric element as a position sensor, positional feedback of wrist rotations may be derived by monitoring the position of the armature of the servo-motors of the prosthesis used to generate the movement of the wrist. Incorporation of a one pulse per unit of rotation encoder into the brush end of the servo-motor may be easily accomplished within the existing dimensional envelope of the prosthesis, without substantial increase of cost, and with no design change to the mechanism, housings or other components of the prosthesis.

Positional feedback of the elbow flexure and the grip closure may also be obtained by the addition of encoders to the servo-motors of the elbow and hand. Incorporation of a one pulse per unit of rotation encoder to the brush end of these servo-motors can also be easily accomplished within the existing dimensional envelope of the prosthesis, without substantial increase of cost, and with no design changes to the mechanism, housings or other components of the prosthesis.

Figure 13:
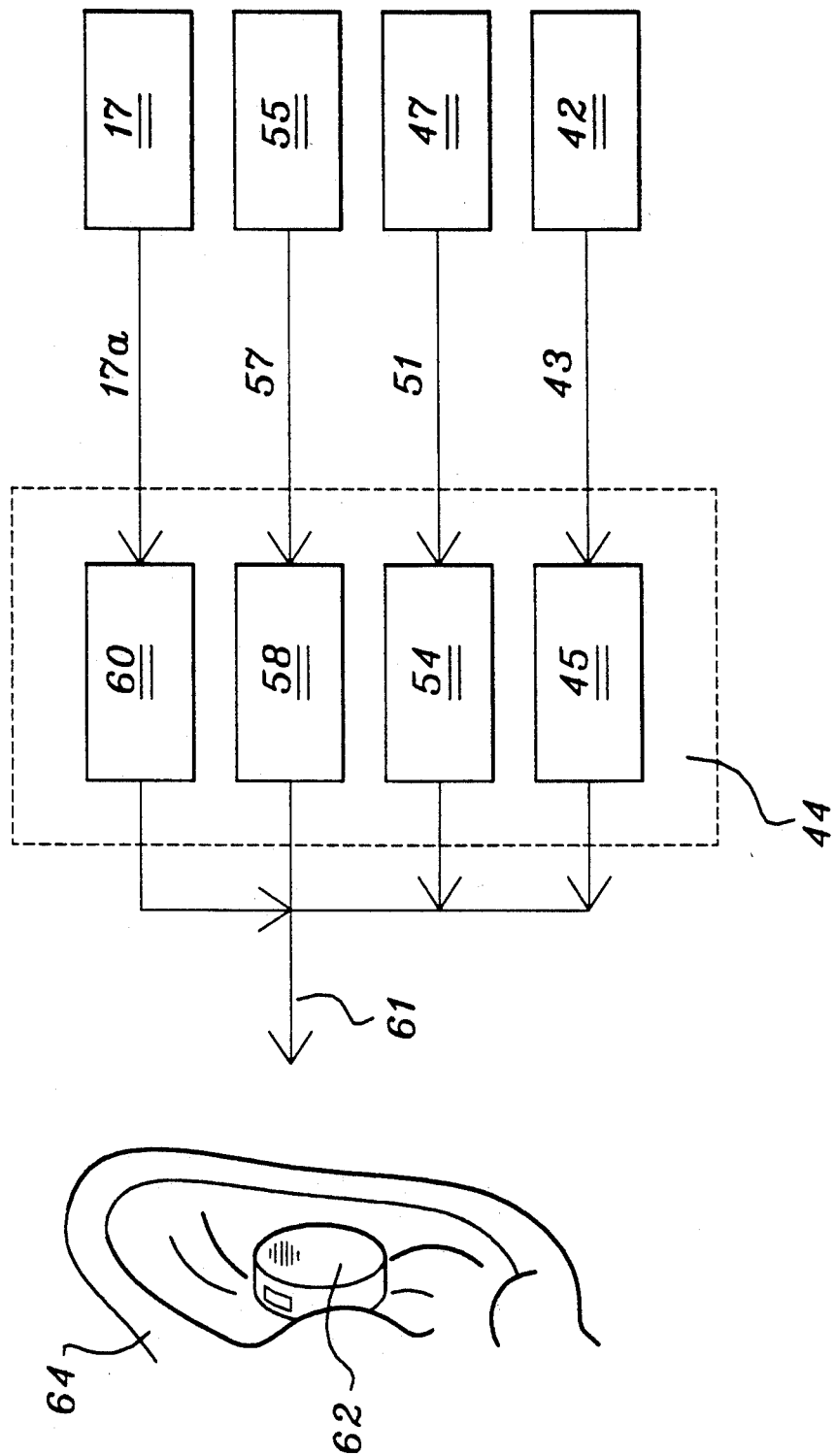
FIG. 13 is a schematic, block diagramic representation of the circuitry employed in connection with the geometry-dependent sensing elements and the audio system associated therewith.
Figure 14:
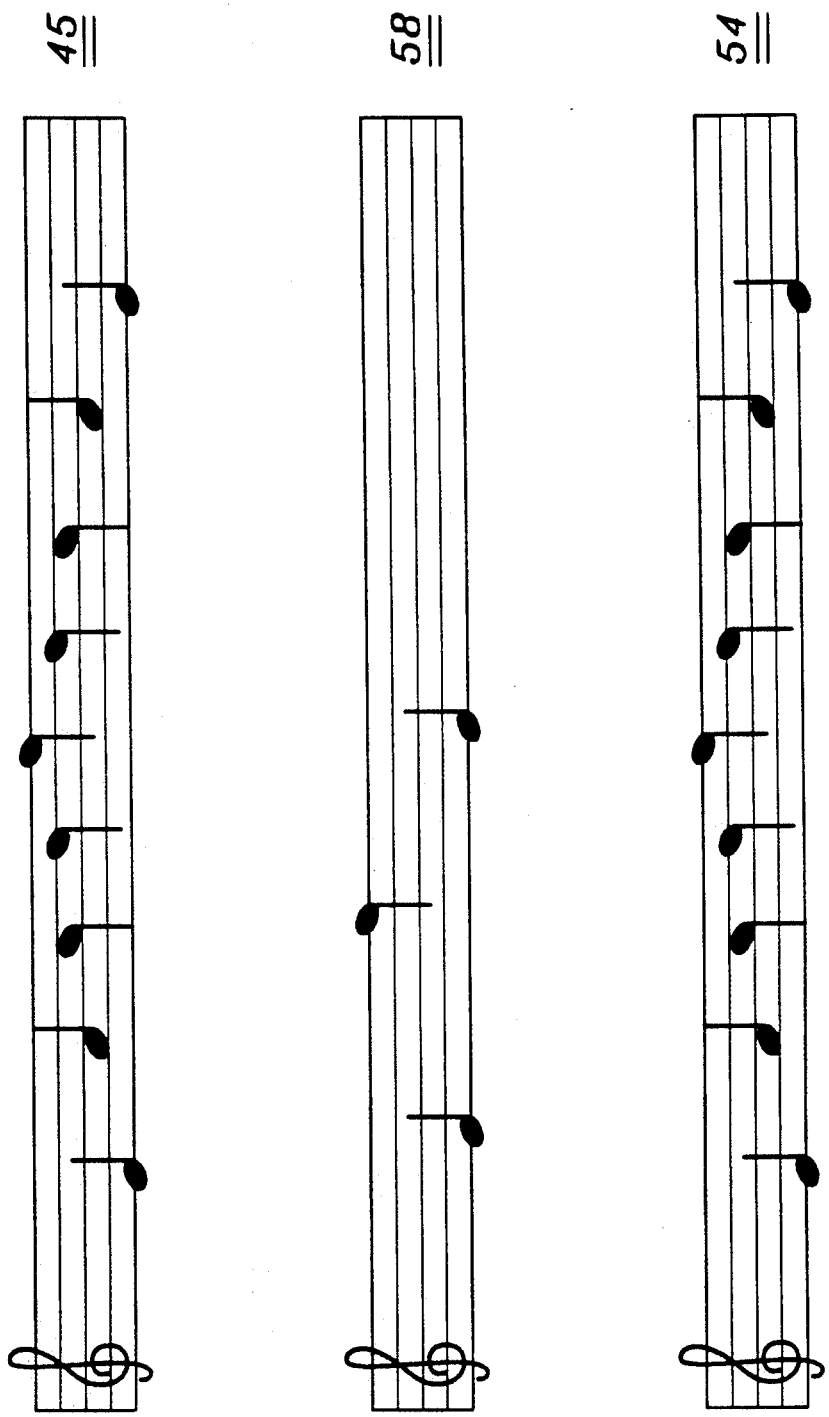
FIG. 14 is a view of the relative musical octaves employed in outputting positional information from the hand, wrist and elbow.

With reference to the block diagrammatic view of FIG. 13 analog outputs 17A of the temperature sensor 17, and positional sensors 42, 47 and 55, of whatever type, are feed to audio system 44 via respective inputs 17A, 43, 51 and 57. Within audio system 44 are provided respective audio chips 60, 45, 54 and 58. Audio chip 60 produces a sound having the pulse-like signal relative to temperature discussed with reference to FIGS. 2C to 2E above. Chips 45, 54 and 58 output respective musical notes 61 within respective octaves (see FIG. 14) which octaves are a function of the anatomical origin thereof, i.e., the hand, elbow or wrist. The specific note within each octave is a function of the orientation of the hand, elbow or wrist, per FIGS. 4 to 12. Accordingly, when the prosthesis is in motion, a series or musical scale of notes within the respective octaves will be heard by an ear piece 62 within the ear 64 of the user.

There is thereby provided a prosthesis capable of providing various patterns of sonic frequency signals corresponding to parameters of pressure (and analogs thereof), temperature (and changes therein), and spatial orientation and twisting of joints (such as the hand and elbow) within a prosthesis. It is believed that such information can be readily integrated into existing state-of-the-art prostheses to achieve a more accurate and advantageous manipulation of existing servo-means and other controls in existent state-of-the-art prosthetic.

While there has been shown and described the preferred embodiment of the instant invention it is to be appreciated that the invention may be embodied otherwise as herein specifically shown and described and that, within said embodiment, certain changes in the detail and construction in the form and arrangement of the parts may be made without departing from the underlying ideal or principles of this invention in the scope of the appended claims.

Having thus described my invention what I claim as new, useful and non-obvious and, accordingly, secure by Letters Patent of the United States is:

1. A sensory input discrimination system for use with a prosthetic limb, the system comprising:
   (a) a plurality of pairs of (i) sonic frequency generators and, in electrical communication therewith, (ii) pressure transducers, said generators and transducers disposed proximally to each other within a corresponding plurality of sites upon said prosthesis, said frequency generators having respective discrete sonic frequencies including a sequence of respectively increasing frequencies, said electrical communication between each of said frequency generators and its corresponding pressure transducer being open in the absence of contact pressure and closed in the presence of contact pressure, in which electrical communication will generate a discrete sonic frequency output from that site to which contact pressure has been applied;
   (b) means for surgical connection of said sonic frequency generators into sonic proximity of vibratory receptors of a bone stump at an amputation site corresponding to the area of connection of the prosthetic limb;
   (c) a plurality of position-dependent electronic means each associated with a bendable joint of interest of the prosthesis, each of said position-dependent means having a characteristic octave of musical notes corresponding to the extent of motion of the corresponding bendable joint, said position-dependent means including means for providing a characteristic audio frequency output within the ear of the user, said output corresponding to the extent of change of position of said joint; and
   (d) means for providing power for the operation of said frequency generators, transducers and position-dependant means, said power unit positioned within said prosthetic limb, whereby said receptors will anatomically generate a neural impulse having a signal pattern correlative to said sonic output frequencies, which neural impulse will anatomically travel from said bone stump to the posterior columns of the spinal cord and, therefrom, to the brain wherein discrimination of such impulse will be accomplished by the brain to recognize the location of pressure, and said audio output will furnish to the ear of the user information regarding the position of the joints of the prosthesis.

2. The system as recited in claim 1 in which the number of said increasing sonic frequencies comprises three.

3. The system as recited in claim 2 in which said sequence of increasing frequencies comprises a generally logarithmically increasing sequence of frequencies.

4. The system as recited in claim 3, comprising:
   (a) a 100 cycles sonic frequency generator disposed within a thumb of said prosthetic limb;
   (b) a 400 cycle sonic frequency generator disposed within an index finger of a hand of said limb; and
   (c) a 700 cycle sonic frequency generator disposed within one of three other digits of said hand of said limb.

5. The system as recited in claim 1 in which said pressure transducers comprise means for analog sensing of pressure.

6. The system as recited in claim 1 further comprising thermal sensing means within sites upon said limb, provided in pulse format to the ear of the user.

7. A positional discrimination system for use with a limb prosthesis, the system comprising:
   (a) position-dependent means placed in said limb prosthesis in operative association with a bendable joint of said prosthesis and including means for providing an output characteristic to the ear of the user as an audio signal corresponding to the extent of change in position of said means;
   (b) means for expressing said audio signal as an octave of musical notes, each of said notes corresponding to respective positions of said joint; and
   (c) means for providing power for the operation of said expressing means of the position-dependent means.

8. The system as recited in claim 7 further comprising;
   a plurality of said position-dependent means placed in each of various joints of the limb, each one of said means having a characteristic musical octave.

9. The system as recited in claim 8 comprising:
   means for combining, within given time domains, more than one musical octave of said output characteristic of said position dependent means.

10. The system as recited in claim 7, further comprising:
    thermal sensing means within sites upon said limb, including audio output means thereof provided to the ear of the user.

11. The system as recited in claim 10, further comprising:

(c) a plurality of pairs of (i) sonic frequency generators and, in electrical communication therewith, (ii) pressure transducers, said generators and transducers disposed proximally to each other within a corresponding plurality of sites upon said prosthesis, said frequency generators having respective discrete sonic frequencies, said electrical communication between each of said frequency generators and its corresponding pressure transducer open in the absence of contact pressure and closed in the presence of contact pressure, in which electrical communication will generate a discrete sonic frequency output from that site to which contact pressure has been applied; and (d) means for surgical connection of said sonic frequency generators into sonic proximity of vibratory receptors of a bone stump at an amputation site corresponding to the area of connection of the prosthetic limb, whereby said receptors will anatomically generate a neural impulse having a signal pattern correlative to said sonic output frequencies, which neural impulses will anatomically travel from said bone stump to the posterior columns of the spinal cord and, therefrom, to the brain wherein discrimination of such impulses will be readily accomplished by the brain to recognize the location of pressure and said audio signal will furnish to the ear information regarding the position of joints of the prosthesis.

12. The system as recited in claim 11 in which said position dependent means comprises a rotational encoder associated with the rotational motion of an axle of a servo-motor of the prosthesis controlling the joint of interest.

* * * * *